(12) United States Patent
Prozzo et al.

(10) Patent No.: US 6,802,871 B1
(45) Date of Patent: Oct. 12, 2004

(54) COMPOSITION FOR PRETREATING FIBER MATERIALS

(75) Inventors: Biancamaria Prozzo, Basel (CH); Peter Seifert, Biberbach (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 174 days.

(21) Appl. No.: 09/688,066

(22) Filed: Oct. 13, 2000

(30) Foreign Application Priority Data

Oct. 16, 1999 (EP) .............................. 99120573

(51) Int. Cl.$^7$ .......................... C11D 17/00; C11D 17/08
(52) U.S. Cl. .............................. 8/139; 8/115.51; 8/909; 8/930; 510/276; 510/426
(58) Field of Search .................... 8/139, 115.51, 8/909, 930, 115.7, 116.1, 181, 188; 510/276, 426

(56) References Cited

U.S. PATENT DOCUMENTS

| | | | |
|---|---|---|---|
| 4,612,352 A | 9/1986 | Schäfer et al. .............. 525/404 |
| 5,002,686 A | 3/1991 | Guth et al. ............ 252/174.16 |
| 5,013,327 A | 5/1991 | Wahle et al. .................. 8/125 |
| 5,456,847 A | 10/1995 | Guth et al. ................... 252/8.9 |
| 5,484,553 A | 1/1996 | Guth et al. .................. 252/351 |
| 5,559,273 A | 9/1996 | Guth et al. .................. 568/622 |
| 5,691,298 A | * 11/1997 | Gosselink et al. .......... 510/475 |
| 5,728,671 A | * 3/1998 | Rohrbaugh et al. ......... 510/394 |
| 5,858,955 A | 1/1999 | Stringer et al. ............. 510/417 |
| 6,004,922 A | * 12/1999 | Watson et al. .............. 510/475 |

FOREIGN PATENT DOCUMENTS

| | | |
|---|---|---|
| EP | 0491531 | 6/1992 |
| EP | 0696661 | 2/1996 |

* cited by examiner

*Primary Examiner*—Margaret Einsmann
*Assistant Examiner*—Preeti Kumar
(74) *Attorney, Agent, or Firm*—Kevin T. Mansfield

(57) ABSTRACT

Compositions which, as well as water, contain certain sulfonate salts or polyhydric alcohols together with ethoxylated/propoxylated alcohols and ethoxylated alcohols are useful for pretreating textile sheet materials. Further ingredients also render them useful for hydrogen peroxide bleaching.

The compositions, which provide the textiles with good primary wettability and good rewettability, are low-foaming. Batchwise pretreatment processes, for example in jet machines, therefore represent no problem.

8 Claims, No Drawings

COMPOSITION FOR PRETREATING FIBER MATERIALS

This invention relates to a composition which includes at least water, an organic sulfonate or a polyhydric alcohol together with an ethoxylated alcohol and an ethoxylated/propoxylated alcohol. It further relates to the use of such compositions for the treatment of fiber materials.

Fiber materials in the form of textile sheet materials, for example woven fabrics, normally have to be subjected to a pretreatment before they are dyed. One purpose of the pretreatment is to ensure a defect-free uniform dyeing. Depending on the prior history and provenience of the textile sheet materials or the equipment available, the pretreatment may include the measures of desizing, degreasing/scouring and bleaching the textiles. These measures may be carried out separately, but in the individual case it is also possible to integrate a plurality of these measures in a single process in order that costs may be saved. A successful pretreatment process requires that the textile be readily wettable by aqueous systems not only at the start of the pretreatment but also after the pretreatment, ie. that the textile possess good primary wettability and good rewettability. The latter ensures trouble-free dyeing. To meet the requirements of a useful pretreatment process, various chemical products are used in the pretreatment. These may include, depending on the stated object, wetting agents, laundry detergents, enzymes, bleaching agents, stabilizers, complexing agents, etc. Particular importance attaches here to products whose task it is to impart good post-pretreatment rewettability on the textile sheet materials. Textiles possessing good rewettability make for uniform dyeing in the subsequent dyeing process. But it is important in this connection that the products responsible for good rewettability should bring about no or only an insignificant increase in the foaming tendency of baths that contain the pretreatment products. This requirement is of particular consequence when the pretreatment is carried out as a batch process, for example in jet machines, where increased foaming can be very troublesome and which are more prone to foaming than other processes. The reason why there is frequently a demand for low-foaming pretreatment products is that it is in many cases undesirable to suppress increased foaming by adding antifoams such as silicones.

Since classic pretreatment steps such as desizing, degreasing/scouring and bleaching are in a number of cases integrated into a combined pretreatment process, there is also a demand for compositions which can be used for such combined pretreatment processes. The compositions have to be aqueous systems that impart good wettability to the textile material at the start of the pretreatment, but also good hydrophilicity at the end of the pretreatment. This good hydrophilicity leads to the good rewettability needed for the dyeing process.

Products for pretreating fiber materials in the form of textile sheet materials are known.

EP-A 98 803 describes graft polymers containing a hydrophobic moiety, an attached polyglycol ether moiety and a hydrophilic graft. The hydrophilic graft may contain ionic groups such as sulfonate or carboxylate radicals or the corresponding acid groups.

EP-A 462 059 reveals textile auxiliaries comprising an alkoxylated and optionally terminally etherified alcohol, a reaction product of such an alcohol and an acidic compound and optionally a hydrotrope. The reaction product from alkoxylated alcohol and acidic compound may be a sulfonate.

WO 92/15664 discloses textile treatment compositions comprising homopolymers of unsaturated sulfonic or carboxylic acids, a nonionic surfactant and optionally a hydrotrope. The surfactant, as with the above-cited EP-A 462 059, is an alkoxylate of an aliphatic alcohol that may also have an organic radical at the other end in place of hydrogen. Such surfactants and their use in textile treatment are also revealed in EP-A 420 802.

EP-A 360 736 describes textile pretreatment compositions comprising a phosphorus compound, an interpolymer having a hydrophilic and hydrophobic moiety, a nonionic surfactant and an alkali metal hydroxide.

The compositions described in the above-cited documents, although in principle suitable for textile pretreatment, do not have optimum properties in every regard. More particularly, the rewettability of the textile material after the pretreatment has been completed presents problems in a number of cases of compositions for the pretreatment of textiles. Good rewettability due to adequate hydrophilicity has to be present after the pretreatment in order that the dyeing properties of the textile may not be adversely affected. True, it is possible in principle to improve rewettability by using the right type and amount of surfactants in the pretreatment. However, it has been determined that such optimization of the rewettability will frequently have an adverse effect on the primary wettability and/or significantly increase foaming. As mentioned, primary wettability denotes the wettability of the textile sheet material at the start of the pretreatment, ie. at the point of first contact of the textile material with the pretreatment liquor. This primary wettability has to reach a certain minimum level in order that the pretreatment can take place without problems. If, then, compositions are used that lead to good rewettability, ie. good wettability after the pretreatment, this will in many cases result in an inadequate primary wettability. Attempts to optimize both primary wettability and rewettability by using correspondingly large amounts of surfactants, by contrast, frequently lead to increased foaming. This increased foaming becomes noticeable especially in pretreatment processes of the batch type, for example in the course of a batchwise pretreatment in jet machines. True, the foam can be controlled by means of silicones, but this is frequently undesirable.

It is an object of the present invention to develop a composition which has excellent utility for the pretreatment of fiber materials, especially textile sheet materials, in that it imparts good primary wettability as well as good rewettability to the textile material and which even without the use of high performance antifoams such as silicones does not produce unacceptable foaming.

This object is achieved by a composition which includes at least the components A, B, C and D, where component A is either a sulfonate of the formula (I)

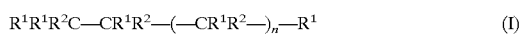

$$R^1R^1R^2C\text{—}CR^1R^2\text{—}(\text{—}CR^1R^2\text{—})_n\text{—}R^1 \qquad (I)$$

where n is from 0 to 8, any $R^1$ is independently of the others hydrogen, an alkyl radical of 1 to 4 carbon atoms, an unsubstituted phenyl radical or a phenyl radical substituted by a radical of the formula $-SO_3^{\ominus}M^{\oplus}$, and any $R^2$ is independently of the others $R^1$ or a radical of the formula $-SO_3^{\ominus}M^{\oplus}$, subject to the proviso that component A contains at least one radical of the formula $-SO_3^{\ominus}M^{\oplus}$ and M is Na, K or $NH_4$, or where component A is a polyhydric aliphatic alcohol of 2 to 12 carbon atoms, preferably of 4 to 10 carbon atoms, component B is an ethoxylated alcohol of the formula (II) or a mixture of such alcohols $$R^3\text{—}O\text{—}(\text{—}CH_2CH_2\text{—}O\text{—})_r\text{—}X \qquad (II)$$

where r is from 1 to 8, preferably from 2 to 7, component C is an alkoxylate of the formula (III) or a mixture of such alkoxylates $$R^3\text{—}O\text{—}(\text{—}Z\text{—})_t\text{—}X \qquad (III)$$

where t is from 4 to 30, preferably from 6 to 18, 20 to 80% of all the Z groups present are —$CH_2CH_2$—O— and 80 to 20% of all the Z groups present are —$CHR^4$—$CHR^5$—O—, where in each case one of $R^4$ and $R^5$ is hydrogen and the other is $CH_3$, $R^3$ in both component B and component C is a linear or branched alkyl radical of 4 to 20, preferably 8 to 18, carbon atoms and 50 to 100%, preferably 100%, of all the X's present are hydrogen and 0 to 50%, preferably 0%, of all the X's present are a methyl, ethyl or phenyl radical, and component D is water.

This abovementioned specific combination of components surprisingly solves a whole series of problems due to prior art textile pretreatment formulations. Such compositions according to the invention are very useful for the pretreatment of textile sheet materials even in cases where a plurality of the pretreatment steps mentioned at the beginning are integrated in a combined process. If they are to be used for hydrogen peroxide bleaching processes as well, however, it is advisable for the compositions to additionally include a component E of the kind more particularly described hereinbelow. The compositions of the invention have advantages especially when they are used for batchwise pretreatment processes, for example in jet machines. They are particularly useful for this on account of their low tendency to foam. They impart to the textiles a high post-pretreatment hydrophilicity, and this manifests itself in an excellent rewettability. The primary wettability of the textiles, ie. the first wettability by the pretreatment liquor at the start of the pretreatment, is likewise very good.

The advantages mentioned are obtained on complying with the specifications set forth in claim 1 and above for the components of the compositions according to the invention.

Component A is either a sulfonate of the formula (I)

$$R^1R^1R^2C\text{—}CR^1R^2\text{—}(\text{—}CR^1R^2\text{—})_n\text{—}R^1 \qquad (I)$$

Here, n is from 0 to 8; in a preferred embodiment, n is from 1 to 3. Any $R^1$ radical is independently of the others hydrogen, a linear or branched alkyl radical of 1 to 4 carbon atoms or a phenyl radical which is either unsubstituted or substituted by a sulfonate radical of the formula —$SO_3^\ominus M^\oplus$. Any $R^2$ radical is independently of the others an $R^1$ radical of the abovementioned kind or a sulfonate radical of the formula —$SO_3^\ominus M^\oplus$. When component A is a compound of the formula (I), however, it shall contain at least one sulfonate radical —$SO_3^\ominus M^\oplus$, ie. either at least one of all the $R^2$ radicals present shall be —$SO_3^\ominus M^\oplus$ or at least one of all the $R^1$ radicals present shall be a phenyl radical which bears an —$SO_3^\ominus M^\oplus$ radical as substituent. In a component A containing one or more phenyl radicals substituted by —$SO_3^\ominus M^\oplus$, the —$SO_3^\ominus M^\oplus$ groups may each be disposed on the aromatic ring in any position. In the —$SO_3^\ominus M^\oplus$ radicals, $M^\oplus$ is in each case a sodium, potassium or ammonium ion. Component A may accordingly be a purely aliphatic or an aliphatic-aromatic hydrocarbon in which one or more —C—H moieties are replaced by —$SO_3^\ominus M^\oplus$ moieties. In a preferred embodiment of compositions according to the invention, component A is a sulfonate of the abovementioned formula (I) where at least one of all the $R^2$ radicals present is —$SO_3^\ominus M^\oplus$. In this case, it can be of advantage for none of the $R^1$ radicals present to contain a sulfonate group. In compositions according to the invention that are particularly useful for the pretreatment of textiles, component A is a sulfonate of the formula (IV)

$$R^6R^7CH\text{—}CR^6R^7\text{—}(\text{—}CR^6R^7\text{—})_w\text{—}H \qquad (IV)$$

where w is from 1 to 3, one of the $R^6$ radicals is an unsubstituted phenyl radical and all the other $R^6$ radicals are hydrogen, and one of the $R^7$ radicals is $SO_3^\ominus M^\oplus$ and all the other $R^7$ radicals are hydrogen. The only phenyl radical present and the only sulfonate radical present may here take the place of any of the $R^6$ and $R^7$ radicals of the formula (IV). Sodium cumenesulfonate and potassium cumenesulfonate are particularly useful as component A in compositions according to the invention.

Instead of a sulfonate of the formula (I), component A in compositions according to the invention may also be polyhydric aliphatic alcohol having 2 to 12, preferably 4 to 10, carbon atoms and a linear or branched carbon chain. It will be appreciated that compositions according to the invention may also include mixtures of sulfonates of the formula (I) and of such polyhydric alcohols. When component A is not a sulfonate but a polyhydric alcohol, a preferred embodiment of compositions according to the invention comprises component A being a dihydric or trihydric aliphatic alcohol having a linear or branched alkyl chain of 4 to 8 carbon atoms. A particularly useful component A is 1,5-pentanediol in which one of the carbon atoms 2 to 4 bears a methyl group as substituent.

Component A must be included in compositions according to the invention. This is because it has been determined that compositions which include water, a component B and a component C but no component A fall short of optimum utility for the pretreatment of textiles. The problem here may be, on the one hand, the rewettability of the textile material after the pretreatment has been carried out: customary amounts of components B and C in the liquors frequently do not provide the required high rewettability performance in the absence of component A. The rewettability problem would in principle be solvable by increasing the amount of compound B and/or C. However, it has been determined that this would necessitate such large amounts that the costs become very high and, in particular, that the foam problem is then no longer controllable without the use of high performance antifoams such as silicones. On the other hand, silicones can have an adverse effect on dyeing characteristics and are therefore undesirable in many cases. Another problem which may arise in the absence of a component A is that it is frequently impossible to obtain a stable liquid, aqueous formulation useful for the treatment of fiber materials and/or that the formulations are excessively prone to foam. Compositions including a component B and a component C and a component D but no component A may take the form of a gel which is not suitable for pretreatment processes. This problem may present itself in the absence of component A even when the abovementioned lack of rewettability would not be a problem in the individual case. However, the use of a component A together with a component B and a component C and water does away with the difficulties discussed here.

Sulfonates and polyhydric alcohols useful as component are commercially available, for example sodium cumenesulfonate, or are preparable according to known chemical methods. Instead of a single compound of the formula (I) or (IV), component A may also be a mixture of such compounds or a mixture of polyhydric alcohols.

Component B in compositions according to the invention is primarily responsible for the primary wettability and the rewettability of the textile sheet materials at the start and on completion of the pretreatment. The pretreatment liquor should wet the textile quickly and uniformly in order that the purpose of the pretreatment may be achieved in optimal fashion. It has been determined that compositions which include a component A and a component C but no component B of the kind mentioned lead to a normally worse primary wettability. Similarly, the rewettability of the fiber materials on completion of the pretreatment may be too low when no component B is included in the compositions.

Component B is an ethoxylated alcohol of the formula (II) or a mixture of such alcohols

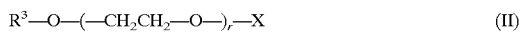

$$R^3-O-(-CH_2CH_2-O-)_r-X \qquad (II)$$

Here, r is from 1 to 8, preferably from 2 to 7. Component B is generally a mixture of ethoxylated alcohols, since ethoxylation reactions as of alcohols with ethylene oxide give rise to product mixtures. In such mixtures, the value of r (the degree of ethoxylation) will vary to a certain extent. For a mixture of ethoxylated products of the formula (II) to be useful as component B in compositions according to the invention, the modal value of r in the mixture must certainly not be greater than 8. It is beneficial when not more than 20% of the molecules in the mixture have r greater than 8; preferably, r is not greater than 7 in not less than 80% of the molecules. It has been determined that ethoxylated alcohols of the formula (II) where r is greater than 8 or where more than 20% of the molecules in the mixture have r greater than 8 are not suitable for use as component B in compositions according to the invention. The reason is that the tendency to foam increases with increasing r and can reach an unacceptable level when r is greater than 8. $R^3$ in the formula (II) is a linear or branched alkyl radical of 4 to 20 carbon atoms. Particular usefulness as component B in compositions according to the invention is possessed by ethoxylated products of the formula (II) where $R^3$ contains 8 to 18 carbon atoms X in the formula (II) can be hydrogen, methyl, ethyl or phenyl. At least 50 to 100% of all X radicals present in component B have to be hydrogen for the required primary wettability to be obtained. So for hydrogen X component B will contain only a single species of ethoxylated molecules of the formula (II). However, since for technical and economic reasons component B will virtually always be a mixture of compounds conforming to the formula (II), the mixture may include compounds where X is hydrogen and compounds where X is $-CH_3$, $-C_2H_5$ or $-C_6H_5$. However, at least 50% of all the X radicals present have to be hydrogen. In a preferred embodiment of compositions according to the invention, however, all the X radicals present in component B are hydrogen even when B is a mixture.

Products of the formula (II) useful as component B are commercially available. They are preparable in a known manner by reacting the corresponding alcohols $R^3$—OH with ethylene oxide with or without subsequent partial etherification of the terminal OH group.

Component C, without being a pronounced antifoam, is a foam-suppressing component and a necessary ingredient of compositions according to the invention. Compositions which include a component A and a component B but no component C can lead to problems in particular when the pretreatment is to be carried out as a batch process in a jet machine. This is because the foam level may then be unacceptably high. Component C is an alkoxylate of the formula (III) or a mixture of such alkoxylates

$$R^3-O-(-Z-)_t-X \qquad (III)$$

Here, $R^3$ and X are each as defined above in connection with component B. Like component B, component C is normally a mixture of products. The ethoxylation/propoxylation of $R^3$—OH alcohols, like the straight ethoxylation, gives rise to product mixtures. The individual compounds of the formula (III) in these mixtures differ with regard to the value of t and/or the number of polyoxyethylene and polyoxypropylene units. Furthermore, the compounds of the formula (III) may be present as block copolymers or as random copolymers, depending on the production conditions. Block polymers are formed for example when $R^3$—OH is reacted first with ethylene oxide only and then—after the ethylene oxide has been consumed—with propylene oxide only. This species of block polymer is preferred for use as component C in compositions according to the invention, optionally after a partial etherification of the terminal OH group. However, it is also possible to use random polymers formed by reaction of $R^3$—OH with a mixture of ethylene oxide and propylene oxide, or partially terminally etherified random polymers. As in the case of component B, 50 to 100%, preferably 100%, of all the X radicals present in component C has to be hydrogen; 0 to 50% of the X radicals can be $-CH_3$, $-C_2H_5$ or $-C_6H_5$.

The degree of ethoxylation/propoxylation of component C is 4 to 30, ie. t in the formula (III) is from 4 to 30. t is preferably a number from 6 to 18. Z in the formula (III) is a divalent polyoxyalkylene radical. 20 to 80% of all the Z radicals present in component C are the radical $-CH_2CH_2-O-$, which is derived from ethylene oxide, while the rest, ie. 80–20% of the Z radicals, are the radical $-CHR^4-CHR^5-O-$, which is derived from propylene oxide and in which one of $R^4$ and $R^5$ is hydrogen while the other is $-CH_3$. The mixture of compounds that is normally component C may include individual molecules in which there are only $-CH_2CH_2-O-$ units between $R^3O$ and X or individual molecules which contain only polyoxypropylene but no polyoxyethylene units. This is inevitable in an industrial ethoxylation/propoxylation. However, the fraction of such molecules in component C is very low, while the substantially predominant fraction, ie. more than 90% of the molecules in component C, contain both polyoxyethylene and polyoxypropylene units.

As in the case of component B, products useful as component C are commercially available or preparable according to generally known methods.

Compositions according to the invention further include water (component D).

Compositions according to the invention are normally preparable without problems by mixing the components A to D and any further desired components in any order by stirring at room temperature. In individual cases, a certain order of mixing and/or a temperature increase may produce benefits with regard to stability in storage. These statements also apply when compositions according to the invention are to include further components, for example the components E and/or F more particularly described hereinbelow.

In a preferred embodiment, compositions according to the invention include a component E and/or a component F as well as the mandatory components A to D. Instead of a single compound, compositions according to the invention may also include mixtures of compounds which fall within the definition of component E and/or F indicated hereinbelow.

Component E is a magnesium salt or a calcium salt, preferably a water-soluble inorganic salt. $MgCl_2$ is particularly suitable. The presence of such a salt can increase the suitability of compositions according to the invention for customary pretreatment processes where the textiles are bleached with $H_2O_2$. These processes require stabilizers for hydrogen peroxide, and the magnesium and calcium salts mentioned may be used for this purpose.

Component F is an alkali metal salt or an ammonium salt of a sulfuric monoester of the formula (V)

$$R^8\text{—O—}SO_3H \qquad (V)$$

ie. a salt of the formula $R^8\text{—O—}SO_3^{\ominus}M^{\oplus}$, where M is Na, K or $NH_4$. $R^8$ in this formula is a linear or branched alkyl radical of 4 to 12, preferably 6 to 10, carbon atoms. The alcohol $R^8\text{—OH}$, from which this monoester salt is derived, can be a primary, secondary or tertiary alcohol, ie. the $\text{—O—}SO_3^{\ominus}M^{\oplus}$ group may be present on any carbon atom in the linear or branched monovalent radical $R^8$. The presence of a component F in compositions according to the invention may enhance the stability of these aqueous compositions.

In a preferred embodiment, compositions according to the invention include the aforementioned components in such amounts that the following amounts of components A, B, C, E and F are present per 100 parts by weight of water (component D):

5 to 35 parts by weight of component A, preferably 10 to 25 parts by weight 10 to 40 parts by weight of component B, preferably 15 to 35 parts by weight 3 to 30 parts by weight of component C, preferably 5 to 25 parts by weight 0 to 30 parts by weight of component E, preferably 2 to 20 parts by weight 0 to 20 parts by weight of component F, preferably 2 to 10 parts by weight If desired, compositions according to the invention may include further ingredients, especially with regard to specific pretreatment processes and requirements. Such ingredients may be for example enzymes, complexing agents or further surfactants; they can be used in the amounts customary for pretreatment processes. However, it is advisable to precede every individual case of the use of such ingredients by an examination as to whether the abovementioned advantages of compositions according to the invention are not unacceptably reduced as a result.

Compositions according to the invention are very useful for treating fiber materials, especially for pretreating textile fiber materials in the form of wovens or knits. The fiber materials in question may be textile sheet materials comprising cellulose, regenerated cellulose or synthetic polymers or blends thereof. Compositions according to the invention are particularly useful for pretreating textile sheet materials which are 70 to 100 percent by weight cotton. The rest of the fibers may be synthetics, for example. A pretreatment of textile sheet materials composed of raw cotton with compositions according to the invention leads to excellent results with regard to primary and rewettability coupled with a tendency to foam which never exceeds an acceptable degree even without the use of high performance antifoams such as silicones. For these reasons, compositions of the invention are also very useful for batchwise pretreatment processes, for example in jet machines.

Compositions according to the invention may be applied to the textile material according to methods customary in pretreatment processes, for example by dipping, pad-mangling, etc. The aqueous liquors used for pretreatment advantageously have customary concentrations, for example from 0.03 to 1 percent by weight of the sum total of components A, B and C, based on total liquor. After the pretreatment, the textile material is further treated in a conventional, known manner, for example by dyeing with or without intermediary drying.

The invention will now be illustrated by examples.

Compositions were prepared in accordance with Table I below, in which the numbers under the respective examples each denote the constituent in question, in % by weight.

TABLE I

| Constituent | Example 1 | Example 2 | Example 3 | Example 4 | Example 5 | Example 6 | Example 7 |
|---|---|---|---|---|---|---|---|
| a) | 6 | — | 6 | 6 | 6 | 6 | 6 |
| b) | 12 | 12 | 12 | 17 | — | — | 12 |
| c) | 6 | 6 | 6 | 6 | 18 | 6 | 6 |
| d) | 25 | 25 | — | 30 | 25 | 25 | — |
| e) | 10 | 10 | 35 | — | 10 | 10 | 10 |
| f) | — | — | — | — | — | 12 | — |
| g) | — | — | — | — | — | — | 25 |
| Water | 41 | 47 | 41 | 41 | 41 | 41 | 41 | a) = magnesium chloride hexahydrate (component E)
b) = sodium cumenesulfonate (component A)
c) = methyl 1,5-pentanediol (component A)
d) = mixture of ethoxylated $C_{13}$ alcohols, 4.6 EO units on average (component B)
e) = ethoxylated/propoxylated alcohol (about $C_{12}$ to $C_{18}$), 8 EO, 4 PO, block copolymer (component C)
f) = R'-$OSO_3$Na
R' = ethylhexyl (component F)
g) = ethoxylated $C_{13}$ alcohol, 10 EO units on average Examples 1, 2, 5 and 6 include a component A), a component B) and a component C), ie. are inventive examples. Examples 3, 4 and 7 are noninventive, comparative examples in that Example 3 lacks a component B, Example 4 lacks a component C and Example 7 has a degree of ethoxylation for the constituent g) that is higher than stipulated for component B.

Compositions #1 to 7 were all tested for primary wettability, rewettability and tendency to foam. Primary wettability was determined on woven samples of 100% raw cotton on the lines of the ISO 8022 method. The time was determined (in seconds) until the fabric had been completely wetted by the composition in question. In Table 2 below, accordingly, lower values for the primary wettability denote better/quicker wetting. The tendency to foam under pretreatment conditions was determined in a laboratory jet apparatus charged in each case with dilute NaOH, $H_2O_2$, a stabilizer for $H_2O_2$ and about 1 g/l of one of the compositions 1 to 7.

In addition, a sample of a 100% cotton knit was put into the apparatus in each case. The contents of the apparatus were mechanically agitated while being heated initially to 40° C. and then to 98° C. and cooled to 80° C. The contents of the apparatus were left to dwell at each of these temperatures for a short time to allow assessment of the amount of foam which had developed. Rewettability was determined by treating the knit samples as indicated above for the determination of foaming. They were then taken from the apparatus and dried. Rewettability was determined by measuring the time (in seconds) within which a drop of water from a dropping pipette completely wetted the fabric.

The results of the tests are shown in Table II.

TABLE II

| | Example 1 | Example 2 | Example 3 | Example 4 | Example 5 | Example 6 | Example 7 |
|---|---|---|---|---|---|---|---|
| Primary wettability (sec) | 15 | 14 | 30 | 15 | 15 | 15 | 15 |
| Re-wettability (sec) | 1 | 1 | 20 | 3 | 1 | 3 | 20 |
| Foaming | minimal | minimal | moderate | very pronounced | minimal | moderate | very pronounced |

What is claimed is:

1. A process for the pretreatment of fiber materials in the form of textile wovens or knits, said process being performed prior to manufacture of enduse articles from said materials, which comprises treating the fiber materials with a composition including at least the components A, B, C and D, where component A is either a sulfonate of the formula (I)

$$R^1R^1R^2C-CR^1R^2-(-CR^1R^2-)_n-R^1 \quad (I)$$

where n is from 0 to 8, each $R^1$ is independently of the others hydrogen, an alkyl radical of 1 to 4 carbon atoms, an unsubstituted phenyl radical or a phenyl radical substituted by a radical of the formula $-SO_3^{\ominus}M^{\oplus}$, and each $R^2$ is independently of the others $R^1$ or a radical of the formula $-SO_3^{\ominus}M^{\oplus}$, subject to the proviso that component A contains at least one radical of the formula $-SO_3^{\ominus}M^{\oplus}$ and M is Na, K or $NH_4$, or where component A is a polyhydric aliphatic alcohol of 2 to 12 carbon atoms, component B is an ethoxylated alcohol of the formula (II) or a mixture of such alcohols $$R^3-O-(-CH_2CH_2-O-)_r-X \quad (II)$$

where r is from 1 to 8, component C is an alkoxylate of the formula (III) or a mixture of such alkoxylates $$R^3-O-(-Z-)_t-X \quad (III)$$

where t is from 4 to 30, 20 to 80% of all the Z groups present are $-CH_2CH_2-O-$ and 80 to 20% of all the Z groups present are $-CHR^4-CHR^5-O-$, where in each case one of $R^4$ and $R^5$ is hydrogen and the other is $CH_3$, $R^3$ in both component B and component C is a linear or branched alkyl radical of 4 to 20 carbon atoms and 50 to 100% of all the X's present are hydrogen and 0 to 50% of all the X's present are a methyl, ethyl or phenyl radical, and component D is water, and optionally also a component E or a component F or a mixture thereof, component E being a magnesium salt or a calcium salt and component F being an alkali metal salt or ammonium salt of a sulfuric monoester of the formula (V)

$$R^8-O-SO_3H \quad (V)$$

where $R^8$ is a linear or branched alkyl radical of 4 to 12 carbon atoms, wherein the composition includes, per 100 parts by weight of water (component D), the following amounts of components A, B, C, E, F: 5 to 35 parts by weight of component A, 10 to 40 parts by weight of component B, 3 to 30 parts by weight of component C, 0 to 30 parts by weight of component E, and 0 to 20 pats by weight of component F.

2. A process according to claim 1, wherein component A is a sulfonate of the formula (I) where at least one of all the $R^2$ radicals present is $-SO_3^{\ominus}M^{\oplus}$.

3. A process according to claim 1, wherein component A is a sulfonate of the formula (IV)

$$R^6R^7CH-CR^6R^7-(-CR^6R^7-)_w-H \quad (IV)$$

where w is from 1 to 3, one of the $R^6$ radicals is an unsubstituted phenyl radical and all the other $R^6$ radicals are hydrogen, and one of the $R^7$ radicals is $-SO_3^{\ominus}M^{\oplus}$ and all the other $R^7$ radicals are hydrogen.

4. A process according to claim 1, wherein component A is sodium cumenesulfonate or potassium cumenesulfonate.

5. A process according to claim 1, wherein component A is a dihydric or trihydric alcohol of 4 to 8 carbon atoms.

6. A process according to claim 1, wherein the fiber materials are 70 to 100% by weight cotton.

7. A process according to claim 1, which is carried out prior to a dyeing step.

8. A process according to claim 1, wherein the composition includes, per 100 parts by weight of water (component D), the following amounts of components A, B, C, E, F:

10 to 25 parts by weight of component A,
15 to 35 parts by weight of component B,
5 to 25 parts by weight of component C,
2 to 20 parts by weight of component E, and
2 to 10 parts by weight of component F.

* * * * *